(12) United States Patent
Holtman et al.

(10) Patent No.: US 9,155,733 B2
(45) Date of Patent: Oct. 13, 2015

(54) **USE OF *TRIS*-QUATERNARY AMMONIUM SALTS AS PAIN MODULATING AGENTS**

(75) Inventors: Joseph R. Holtman, Lexington, KY (US); Peter Anthony Crooks, Nicholasville, KY (US); Linda P. Dwoskin, Lexington, KY (US); J. Michael McIntosh, Salt Lake City, UT (US)

(73) Assignees: University of Kentucky Research Foundation, Lexington, KY (US); University of Utah, Salt Lake City, UT (US)

( * ) Notice: Subject to any disclaimer, the term of this patent is extended or adjusted under 35 U.S.C. 154(b) by 623 days.

(21) Appl. No.: 12/576,300

(22) Filed: Oct. 9, 2009

(65) Prior Publication Data

US 2010/0120857 A1    May 13, 2010

Related U.S. Application Data (60) Provisional application No. 61/195,824, filed on Oct. 10, 2008.

(51) Int. Cl.
*A01N 43/42* (2006.01)
*A61K 31/47* (2006.01)
*A61K 31/4709* (2006.01)

(52) U.S. Cl.
CPC ................................ *A61K 31/4709* (2013.01)

(58) Field of Classification Search
None
See application file for complete search history.

(56) References Cited

U.S. PATENT DOCUMENTS

| 5,691,365 A | 11/1997 | Crooks et al. | |
|---|---|---|---|
| 2003/0225142 A1 | 12/2003 | Crooks et al. | |
| 2005/0261334 A1 | 11/2005 | Crooks et al. | |
| 2006/0247270 A1 * | 11/2006 | Mazurov et al. | 514/305 |
| 2011/0105556 A1 | 5/2011 | Crooks et al. | |
| 2013/0030018 A1 | 1/2013 | Crooks et al. | |
| 2014/0080866 A1 | 3/2014 | Crooks et al. | |

FOREIGN PATENT DOCUMENTS

WO    WO 2007076112 A2 *    7/2007

OTHER PUBLICATIONS

Finnerup et al. (Fundamental & Clinical Paramacology, 2007, 21, 129-136).*
Written Opinion (PCT/ISA/237) dated Sep. 25, 2008 (six (6) pages).
International Preliminary Report on Patentability dated Nov. 4, 2008 (seven (7) pages).
Itahara et al., "Molecular assemblies of bis- and tris-adenine derivatives," Journal of Molecular Structure, 2002, pp. 213-220, vol. 616, Elsevier (eight (8) pages).
Levin et al., "The nicotinic antagonist mecamylamine preferentially inhibits cocaine vs. food self-administration in rats," Physiology & Behavior, 2000, pp. 565-570, vol. 71, Elsevier (six (6) pages).
Berge et al., "Pharmaceutical Salts, Journal of Pharmaceutical Sciences," 1977, pp. 1-19, vol. 66, No. 1, (nineteen (19) pages).

* cited by examiner

*Primary Examiner* — Dennis Heyer
*Assistant Examiner* — Daniel M Podgorski
(74) *Attorney, Agent, or Firm* — Crowell & Moring LLP (57) ABSTRACT

Provided are tris-quaternary ammonium compounds which are modulators of nociception and pain.

7 Claims, 2 Drawing Sheets

USE OF TRIS-QUATERNARY AMMONIUM SALTS AS PAIN MODULATING AGENTS

FIELD OF THE INVENTION

The invention relates to the use of tris-quaternary ammonium salts for pain modulation.

BACKGROUND OF THE INVENTION

The treatment of pain is a critical health issue. Acute (eg. postoperative pain) and chronic (eg. arthritis, low back, cancer) pain affects tens of millions of people annually in the US. Each year some 30 million people visit a physician with a complaint of a painful condition. Some 10% of these patients are seen with chronic pain as their main complaint. The financial loss due to pain has been estimated to exceed 100 billion dollars a year as a result of medical fees, decreased productivity, litigation and the cost of drugs. New therapeutic agents with greater efficacy, in particular for chronic neuropathic pain syndromes (eg. complex regional pain syndrome), and with fewer side effects would result in significant societal benefit.

Pain can be broadly divided into two categories: nociceptive and neuropathic pain. Nociceptive pain occurs as a result of activation of peripheral nociceptors, actually free nerve endings by noxious stimuli (heat, pressure, inflammatory mediators). Examples of nociceptive pain include postsurgical pain, inflammatory pain (eg. arthritis) and low back pain. Such a pain is often described as "a constant, dull, aching pain". Neuropathic pain occurs as a result of damage to the peripheral or central nervous system. Examples of neuropathic pain include radiculopathy (eg. disc impingement on a nerve), complex regional pain syndrome (CRPS I, II), diabetic peripheral neuropathy or central pain (stroke, spinal cord injury, multiple sclerosis). Patients typically describe neuropathic pain as "burning and tingling" in nature. It is characterized by hyperalgesia (increased painful response to a noxious stimulus) and allodynia (pain to a previously non-noxious stimulus).

In many patients, in particular those with chronic pain conditions of malignant (cancer-related pain) and non-malignant (arthritis, low back pain, CRPS) origin, pain is inadequately managed with currently available drugs. Available drugs are simple modifications (eg. extended release) of drugs from classes which have been available for decades including the opioids, nonsteroidal anti-inflammatory agents (NSAID's) or various adjuvants (antidepressants, anticonvulsants) initially approved for other uses besides pain. Opioids (eg. morphine, oxycodone) are often successfully used for the treatment of moderate to severe nociceptive pain. Chronic neuropathic pain is much less responsive to opioids. Use of opioid analgesics is associated with a broad range of significant side effects including cognitive impairment, respiratory depression and constipation. In addition, long-term opioid dosing results in the development of tolerance to the analgesic effect, drug abuse and dependence. The NSAID's (eg. ibuprofen) act by inhibition of the cyclo-oxygenase (Cox-1,2) enzyme. They are especially useful in nociceptive pain of inflammatory origin (eg. arthritis). However, the NSAID's have limited efficacy when compared to the opioids. In addition, NSAID's have significant side effects (renal, gastrointestinal, cardiovascular). The discovery of the Cox-2 selective agents (eg. rofecoxib-Vioxx®; celecoxib-Celebrex®; valdecoxib-Bextra®) which have far less gastrointestinal toxicity, was thought to be an advance in NSAID pharmacology. Nonetheless, these agents still have low efficacy and evidence is now available linking them to significant cardiovascular events including stroke and myocardial infarction following chronic use. This has resulted in the removal of both rofecoxib and valdecoxib from the market. No suitable agent exists for the treatment of neuropathic pain. GABA-pentin (Neurontin®), an anticonvulsant, has found use for some neuropathic pain syndromes (eg. diabetic peripheral neuropathy, postherpetic neuralgia), but it still has limited efficacy. Duloxetine (Cymbalta®), an antidepressant, has recently been approved for the treatment of diabetic peripheral neuropathy. However, it has limited efficacy and usefulness for other neuropathic pain states. The N-methyl-d-aspartate (NMDA) receptor antagonists (eg. ketamine) have been proposed for the treatment of neuropathic pain. Their general use is impractical given the marked side effects including sedation, psychosis and motor impairment. The limitations of the currently available therapies clearly demonstrate the need for a broad spectrum new class of efficacious and safe analgesic drugs for the treatment of nociceptive and neuropathic pain.

Given the need for more effective, less toxic, analgesic drugs, a great deal of emphasis has been placed on identifying novel molecular targets that could form the basis for new analgesics.

SUMMARY OF INVENTION

In one embodiment, compounds corresponding to the following structure are provided.

(I)

The three side chains attached to the phenyl ring can be connected to the 1, 2, and 3 positions; the 1, 2, and 4 positions; or the 1, 3 and 5 positions of the phenyl ring.

The values for m1, m2 and m3 are each independently 0, 1, 2, 3, 4 or 5.

The values for n1, n2, and n3 are each independently 1, 2, 3, 4 or 5.

$X^{1\ominus}$, $X^{2\ominus}$, and $X^{3\ominus}$ are each independently an organic or inorganic anion.

$L^1$, $L^2$ and $L^3$ are each independently chosen from the group consisting of —$CH_2$—$CH_2$—, cis —CH=CH—, trans —CH=CH—, —C≡C—, —$CH_2$—S—, —S—$CH_2$—, —Se—$CH_2$—, —$CH_2$—Se—, —$CH_2$—O—, —O—$CH_2$—, —$CH_2$—NH—, —NH—$CH_2$—, —$CH_2$—NR— where R is a branched or straight chain alkyl group of one to four carbons, —NR—$CH_2$— where R is a branched or straight chain alkyl group of one to four carbons, —CH=N—, —N=CH—, and —N=N—.

$R^1$, $R^2$, and $R^3$ are each independently five or six membered nitrogen containing rings as shown in formulas (IIA) and (IIB).

$A^1$ is carbon or nitrogen, provided that when $A^1$ joins a ring atom with an unsaturated bond or is a nitrogen, $R^9$ is absent, and when $A^1$ joins a ring atom an unsaturated bond and is a nitrogen, both $R^4$ and $R^9$ are absent.

$A^2$ is carbon or nitrogen, provided that when $A^2$ joins a ring atom an unsaturated bond or is a nitrogen, $R^{10}$ is absent, and when $A^2$ joins a ring atom an unsaturated bond and is a nitrogen, both $R^5$ and $R^{10}$ are absent.

$A^3$ is carbon or nitrogen, provided that when $A^3$ joins a ring atom an unsaturated bond or is a nitrogen, $R^{11}$ is absent, and when $A^3$ joins a ring atom an unsaturated bond and is a nitrogen, both $R^6$ and $R^{11}$ are absent.

$A^4$ is carbon or nitrogen, provided that when $A^4$ joins a ring atom an unsaturated bond or is a nitrogen, $R^{12}$ is absent, and when $A^4$ joins a ring atom an unsaturated bond and is a nitrogen, both $R^7$ and $R^{12}$ are absent.

$A^5$ is carbon or nitrogen, provided that when $A^5$ joins a ring atom an unsaturated bond or is a nitrogen, $R^{13}$ is absent, and when $A^5$ joins a ring atom an unsaturated bond and is a nitrogen, both $R^8$ and $R^{13}$ are absent.

$A^6$ is carbon or nitrogen, provided that when $A^6$ joins a ring atom an unsaturated bond or is a nitrogen, $R^{19}$ is absent, and when $A^6$ joins a ring atom an unsaturated bond and is a nitrogen, both $R^{15}$ and $R^{19}$ are absent.

$A^7$ is carbon or nitrogen, provided that when $A^7$ joins a ring atom an unsaturated bond or is a nitrogen, $R^{20}$ is absent, and when $A^7$ joins a ring atom an unsaturated bond and is a nitrogen, both $R^{16}$ and $R^{20}$ are absent.

$A^8$ is carbon or nitrogen, provided that when $A^8$ joins a ring atom an unsaturated bond or is a nitrogen, $R^{21}$ is absent, and when $A^8$ joins a ring atom an unsaturated bond and is a nitrogen, both $R^{17}$ and $R^{21}$ are absent.

$A^9$ is carbon or nitrogen, provided that when $A^9$ joins a ring atom an unsaturated bond or is a nitrogen, $R^{22}$ is absent, and when $A^9$ joins a ring atom an unsaturated bond and is a nitrogen, both $R^{18}$ and $R^{22}$ are absent.

$R^{14}$ or $R^{23}$ is absent when any of the bonds to the ammonium nitrogen is unsaturated, and $R^{14}$ or $R^{23}$ is a straight chain or branched alkyl group of four carbons or fewer when all of the bonds to the ammonium nitrogen are saturated.

$R^4$, $R^5$, $R^6$, $R^7$, $R^8$, $R^9$, $R^{10}$, $R^{11}$, $R^{12}$, and $R^{13}$ or $R^{15}$, $R^{16}$, $R^{17}$, $R^{18}$, $R^{19}$, $R^{20}$, $R^{21}$, and $R^{22}$, when present, are each independently selected from hydrogen; alkyl; substituted alkyl; cycloalkyl; substituted cycloalkyl; alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; halo; cyano; nitro; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur; or $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight member cyclolkane, substituted cycloalkane, cycloalkene, substituted cycloalkene, aryl, substituted aryl, heterocycle with one to three hetero atoms in the ring, or substituted heterocycle with one to three hetero atoms in the ring.

In another embodiment, describes tris-quaternary ammonium compounds as described above which are modulators of nociception and pain.

In another embodiment, a composition is provided comprising a pharmaceutically acceptable carrier and a compound as described above.

In another embodiment, a method is provided for preventing and/or treating nociception and pain and associated disorders comprising administering a therapeutically effective amount of a compound as described above to a mammalian subject in need thereof.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

Before the present compositions and methods are described, it is to be understood that the invention is not limited to the particular methodologies, protocols, assays, and reagents described, as these can vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "alkylaryl" refers to alkyl-substituted aryl groups, and "substituted alkylaryl" refers to alkylaryl groups further bearing one or more substituents as set forth above.

The term "arylalkyl" refers to aryl-substituted alkyl groups, and "substituted arylalkyl" refers to arylalkyl groups further bearing one or more substituents as set forth above.

The term "arylalkenyl" refers to aryl-substituted alkenyl groups, and "substituted arylalkenyl" refers to arylalkenyl groups further bearing one or more substituents as set forth above.

The term "arylalkynyl" refers to aryl-substituted alkynyl groups, and "substituted arylalkynyl" refers to arylalkynyl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "acyl" refers to alkyl-carbonyl groups, and "substituted acyl" refers to acyl groups further bearing one or more substituents as set forth above.

The term "halogen" refers to fluoride, chloride, bromide or iodide groups.

It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are tris-quaternary ammonium salts corresponding to Formula (I):

$$X^{2\ominus} \oplus R^2-(CH_2)_{n2}-L^2-(CH_2)_{m2}$$
$$\phantom{X^{2\ominus} \oplus R^2-(CH_2)_{n2}-L^2-}\bigg\langle\phantom{Ph}\bigg\rangle-(CH_2)_{m1}-L_1-(CH_2)_{n1}-R_1\oplus \ominus X_1$$
$$X^{3\ominus} \oplus R^3-(CH_2)_{n3}-L^2-(CH_2)_{m2}$$

(I)

The three side chains attached to the phenyl ring can be connected to the 1, 2, and 3 positions; the 1, 2, and 4 positions; or the 1, 3 and 5 positions of the phenyl ring.

The values for m1, m2 and m3 are each independently 0, 1, 2, 3, 4 or 5.

The values for n1, n2, and n3 are each independently 1, 2, 3, 4 or 5.

$X^{1\ominus}$, $X^{2\ominus}$, and $X^{3\ominus}$ are each independently an organic or inorganic anion.

$L^1$, $L^2$ and $L^3$ are each independently chosen from the group consisting of —$CH_2$—$CH_2$—, cis —CH=CH—, trans —CH=CH—, —C≡C—, —$CH_2$—S—, —S—$CH_2$—, —Se—$CH_2$—, —$CH_2$—Se—, —$CH_2$—O—, —O—$CH_2$—, —$CH_2$—NH—, —NH—$CH_2$—, —$CH_2$—NR— where R is a branched or straight chain alkyl group of one to four carbons, —NR—$CH_2$— where R is a branched or straight chain alkyl group of one to four carbons, —CH=N—, —N=CH—, and —N=N—.

$R^1$, $R^2$, and $R^3$ are each independently five or six membered nitrogen containing rings as shown in formulas (IIA) and (IIB).

(IIA)

(IIB)

$A^1$ is carbon or nitrogen, provided that when $A^1$ joins a ring atom with an unsaturated bond or is a nitrogen, $R^9$ is absent, and when $A^1$ joins a ring atom with an unsaturated bond and is a nitrogen, both $R^4$ and $R^9$ are absent.

$A^2$ is carbon or nitrogen, provided that when $A^2$ joins a ring atom with an unsaturated bond or is a nitrogen, $R^{10}$ is absent, and when $A^2$ joins a ring atom with an unsaturated bond and is a nitrogen, both $R^5$ and $R^{10}$ are absent.

$A^3$ is carbon or nitrogen, provided that when $A^3$ joins a ring atom with an unsaturated bond or is a nitrogen, $R^{11}$ is absent, and when $A^3$ joins a ring atom with an unsaturated bond and is a nitrogen, both $R^6$ and $R^{11}$ are absent.

$A^4$ is carbon or nitrogen, provided that when $A^4$ joins a ring atom with an unsaturated bond or is a nitrogen, $R^{12}$ is absent, and when $A^4$ joins a ring atom with an unsaturated bond and is a nitrogen, both $R^7$ and $R^{12}$ are absent.

$A^5$ is carbon or nitrogen, provided that when $A^5$ joins a ring atom with an unsaturated bond or is a nitrogen, $R^{13}$ is absent, and when $A^5$ joins a ring atom with an unsaturated bond and is a nitrogen, both $R^8$ and $R^{13}$ are absent.

$A^6$ is carbon or nitrogen, provided that when $A^6$ joins a ring atom with an unsaturated bond or is a nitrogen, $R^{19}$ is absent, and when $A^6$ joins a ring atom with an unsaturated bond and is a nitrogen, both $R^{15}$ and $R^{19}$ are absent.

$A^7$ is carbon or nitrogen, provided that when $A^7$ joins a ring atom with an unsaturated bond or is a nitrogen, $R^{20}$ is absent, and when $A^7$ joins a ring atom with an unsaturated bond and is a nitrogen, both $R^{16}$ and $R^{20}$ are absent.

$A^8$ is carbon or nitrogen, provided that when $A^8$ joins a ring atom with an unsaturated bond or is a nitrogen, $R^{21}$ is absent, and when $A^8$ joins a ring atom with an unsaturated bond and is a nitrogen, both $R^{17}$ and $R^{21}$ are absent.

$A^9$ is carbon or nitrogen, provided that when $A^9$ joins a ring atom with an unsaturated bond or is a nitrogen, $R^{22}$ is absent, and when $A^9$ joins a ring atom with an unsaturated bond and is a nitrogen, both $R^{18}$ and $R^{22}$ are absent.

$R^{14}$ or $R^{23}$ is absent when any of the bonds to the ammonium nitrogen is unsaturated, and $R^{14}$ or $R^{23}$ is a straight chain or branched alkyl group of four carbons or fewer when all of the bonds to the ammonium nitrogen are saturated.

$R^4 R^5$, $R^6$, $R^7$, $R^8$, $R^9$, $R^{10}$, $R^{11}$, $R^{12}$, and $R^{13}$ or $R^{15}$, $R^{16}$, $R^{17}$, $R^{18}$, $R^{19}$, $R^{20}$, $R^{21}$, and $R^{22}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur; or $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight member cyclolkane, substituted cycloalkane, cycloalkene, substituted cycloalkene, aryl, substituted aryl, heterocycle with one to three hetero atoms in the ring, or substituted heterocycle with one to three hetero atoms in the ring.

For example, $R^1$, $R^2$, and $R^3$ include pyrrole, pyrrolidine, pyrazole, imidazole, 1,2,3-triazole, 1,2,4-triazole, pyridine, piperidine, quinoline, tetrahydroquinoline, isoquinoline, tetrahydroisoquinoline, pyrazine, piperazine, pyridazine, and triazine.

As another example, $R^4 R^5$, $R^6$, $R^7$, $R^8$, $R^9$, $R^{10}$, $R^{11}$, $R^{12}$, and $R^{13}$ or $R^{15}$, $R^{16}$, $R^{17}$, $R^{18}$, $R^{19}$, $R^{20}$, and $R^{22}$, include hydrogen, methyl, ethyl, propyl, butyl, trifluoromethyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo[3.2.1]octane, 1-aza-bicyclo[2.2.1]heptane, 8-methyl-8-aza-bicyclo[3.2.1]octane, 1-aza-tricyclo[3.3.1.1$^{3,7}$]decane, methyl cycloalkyl, methyl substituted cycloalkyl, methylpyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-aza-bicyclo[3.2.1]octane, methyl-1-aza-bicyclo[2.2.1]heptane, 8-methyl-8-aza-bicyclo[3.2.1]octane, and methyl-1-aza-tricyclo[3.3.1.1$^{3,7}$]decane.

As a further example, when $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight-membered ring, that ring can be a heterocycle containing up to three hetero atoms (for example nitrogen, oxygen or sulfur) in the ring, and further can be substituted with one or more substituents. For example, possible rings include benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pynrole, indazole, indoxazine, benzoxazole, anthranil naphthalene, tetralin, decalin, chromene, coumarin, chroman-4-one, isocoumarin, isochromen-3-one, quinoline, isoquinoline, cinnoline, quinazoline, naphthyrdine, pyrido[3,4-b]-pyridine, pyridol[3,2-b]pyridine, pyrido[4,3,-b]-pyridine, benzoxazine, anthracene, phenanthrene, phenalene, fluorene, carazole, xanthene, acnidine, octahydro-[1]pyridine, 1-methyloctahydro-[1]pyridine, octahydroindole, 1-methyloctahydro-indole, octahydro-cyclopenta[b]pyrrole, 1-methyloctahydrocyclopenta[b]pyrrole, decahydroquinoline, and 1-methyldecahydroquinoline.

$X^{1\ominus}$, $X^{2\ominus}$, and $X^{3\ominus}$, for example, include F$^-$, Cl$^-$, Br$^-$, I$^-$, NO$_2^-$, HSO$_4^-$, SO$_4^-$, HPO$_4^-$, PO$_4^{2-}$, methanesulfonate, trifluoromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms can be in some cases hydrates or solvates with alcohols and other solvents.

In a compound of Formula (I), preferably the phenyl ring is substituted at the 1, 3 and 5 positions.

In a compound of Formula (I), preferably $A^1$, $A^2$, $A^3$, $A^4$, and $A^5$ are carbon.

In a compound of Formula (I), preferably $R^1$, $R^2$, and $R^3$ are substituted, six-membered, aromatic rings. More preferably, $R^1$, $R^2$, and $R^3$ are substituted pyridinium rings.

In a compound of Formula (I), preferably $R^4$ is hydrogen, alkyl, or forms an aryl ring with $A^1$, $A^2$ and $R^5$. More preferably, $R^4$ is hydrogen, methyl or forms a phenyl group with $A^1$, $A^2$ and $R^5$.

In a compound of Formula (I), preferably $R^5$ is hydrogen, alkyl, phenyl, 1-methyl-2-pyrrolidinyl, forms a six-membered ring with $A^1$, $A^2$ and $R^4$, or forms an aryl ring with $A^2$, $A^3$ and $R^6$. More preferably, $R^5$ is hydrogen, methyl, butyl, phenyl, 1-methyl-2-pyrrolidinyl, forms a phenyl group with $A^1$, $A^2$ and $R^4$, or forms a phenyl group with $A^2$, $A^3$ and $R^6$.

In a compound of Formula (I), preferably $R^6$ is hydrogen, alkyl, or forms an aryl ring with $A^2$, $A^3$ and $R^5$. More preferably, $R^6$ is hydrogen, methyl or forms a phenyl group with $A^2$, $A^3$ and $R^5$.

In a compound of Formula (I), preferably $R^7$ is hydrogen or alkyl. More preferably, $R^7$ is hydrogen or methyl.

In a compound of Formula (I), preferably $R^8$ is hydrogen.
In a compound of Formula (I), preferably m=0.
In a compound of Formula (I), preferably n=3.
In a compound of Formula (I), preferably $L^1$, $L^2$ and $L^3$ are —CH$_2$—CH$_2$— or —C≡C—.

In a compound of Formula (I), preferably $X^{1\ominus}$, $X^{2\ominus}$, and $X^{3\ominus}$ are halogens. More preferably, $X^{1\ominus}$, $X^{2\ominus}$, and $X^{3\ominus}$ are bromide.

In one embodiment, the compound of Formula (I) is defined wherein the phenyl ring is 1,3,5 substituted; wherein m=0; wherein n=3; wherein L is —CH$_2$CH$_2$— or —C≡C—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

In another embodiment, the compound of Formula (I) is defined wherein the phenyl ring is 1,3,5 substituted; wherein m=0; wherein n=3; wherein L is —CH$_2$CH$_2$—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

In another embodiment, the compound of Formula (I) is defined wherein the phenyl ring is 1,3,5 substituted; wherein m=0; wherein n=3; wherein L is —C≡C—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

An exemplary compound for this application is presented below:

The compounds of the present invention can contain one or more stereocenters. The invention includes all possible diastereomers and all enantiomeric forms as well as racemic mixtures. The compounds can be separated into substantially optically pure compounds.

Central nervous system disorders which can be treated according to the method of the present invention include disorders of nociception, and pain.

In yet another embodiment, the present invention is directed to a method for preventing pain, comprising administering to a mammalian subject in need thereof a therapeutically effective amount of a compound of Formula (I). In such a method, the compound of Formula (I) can reduce a pain response.

The compounds of the present invention can be delivered directly or in pharmaceutical compositions along with suitable carriers or excipients, as is well known in the art. For example, a pharmaceutical composition of the invention can include a conventional additive, such as a stabilizer, buffer, salt, preservative, filler, flavor enancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration can, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof can be administered sublingually or via a spray. The agent or composition thereof can be administered in a local rather than a systemic manner. For example, a suitable agent can be delivered via injection or in a targeted drug delivery system, such as a depot or sustained release formulation.

The pharmaceutical compositions of the present invention can be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition can be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds can also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Also, wetting agents such as sodium dodecyl sulfate can be included.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In one embodiment, the compounds of the present invention can be administered transdermally, such as through a skin patch, or micro-needle patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit can be determined by providing a valve to deliver a metered amount. Capsules and cartridges of, for example, gelatin, for use in an inhaler or insufflator can be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Formulations for parenteral administration include aqueous solutions or other compositions in water-soluble form.

Suspensions of the active compounds can also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

As mentioned above, the compositions of the present invention can also be formulated as a depot preparation. Such long acting formulations can be administered by implantation (for example, subcutaneously or intramuscularly) or by intramuscular injection. Thus, for example, the present compounds can be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) consists of VPD diluted 1:1 with a 5% dextrose in water solution. This co-solvent system is effective in dissolving hydrophobic compounds and produces low toxicity upon systemic administration. Naturally, the proportions of a co-solvent system can be varied considerably without destroying its solubility and toxicity characteristics. Furthermore, the identity of the co-solvent components can be varied. For example, other low-toxicity nonpolar surfactants can be used instead of polysorbate 80, the fraction size of polyethylene glycol can be varied, other biocompatible polymers can replace polyethylene glycol, e.g., polyvinyl pyrrolidone, and other sugars or polysaccharides can substitute for dextrose.

Alternatively, other delivery systems for hydrophobic molecules can be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also can be employed, although usually at the cost of greater toxicity. Additionally, the compounds can be delivered using sustained-release systems, such as semi-permeable matrices of solid hydrophobic polymers containing the effective amount of the composition to be administered. Various sustained-release materials are established and available to those of skill in the art. Sustained-release capsules can, depending on their chemical nature, release the compounds for a few weeks up to over 100 days. Depending on the chemical nature and the biological stability of the therapeutic reagent, additional strategies for stabilization can be employed.

For any composition used in the present methods of treatment, a therapeutically effective dose can be estimated initially using a variety of techniques well known in the art. Dosage ranges appropriate for human subjects can be determined, for example, using data obtained from animal studies.

A therapeutically effective dose of an agent refers to that amount of the agent that results in amelioration of symptoms.

Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages can vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions can, if desired, be presented in a pack or dispenser device containing one or more unit dosage forms containing the active ingredient. Such a pack or device can, for example, comprise metal or plastic foil, such as a blister pack. The pack or dispenser device can be accompanied by instructions for administration. Compositions comprising a compound of the invention formulated in a compatible pharmaceutical carrier can also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following example, which is intended to be purely exemplary of the invention. The present invention is not limited in scope by the exemplified embodiment, which is intended as an illustration of a single aspect of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Preparation of
1,3,5-tris-(5-hydroxypent-1-ynyl)-benzene

-continued 1,3,5-Tribromobenzene (10 g, 31.76 mmol), 4-pentyn-1-ol (10.69 g, 127.06 mmol) and bis(triphenylphosphine)palladium(II) dichloride were stirred in triethylamine under nitrogen for 5 minutes. Copper(I) iodide (92 mg, 0.48 mmol) was added and the mixture was stirred for 6 hours at 80° C. The mixture was cooled to room temperature, filtered through a celite pad and rinsed with ethyl acetate. The combined filtrate was evaporated to dryness under reduced pressure. The resulting residue was purified by column chromatography (CHCl$_3$:MeOH 10:1) to afford 7.61 g of 1,3,5-tris-(5-hydroxy-1-pentynyl)benzene. Yield: 74%. $^1$H NMR (300 MHz, CDCl$_3$) δ 7.31 (3, 3 h), 3.81 (t, J=6.0 Hz, 6H), 2.52 (t, J=6.9 Hz, 6H), 1.85 (m, 6H); $^{13}$C NMR (75 MHz, CDCl$_3$) δ 133.8, 124.2, 90.5, 80.0, 61.9, 31.5, 16.2 ppm.

Example 2

Preparation of 1,3,5-tris-(5-hydroxypentyl)benzene 1,3,5-tris-(5-hydroxy-1-pentynyl)benzene (2.84 g, 8.6 mmol) was dissolved in methanol (30 mL) and 10% Pd/C (5% w/w) was added. The resulting mixture was hydrogenated on a Parr hydrogenation apparatus (45 psi) for 4 hours. The catalyst was removed by filtration through a celite pad. The filter cake was rinsed with methanol, and the combined organic liquors were concentrated under reduced pressure. The crude product was purified by column chromatography (CHCl$_3$:MeOH 6:1) to afford 2.84 g of 1,3,5-tris-(5-hydroxypentyl)benzene. Yield 96%. $^1$H NMR (300 MHz, CDCl$_3$) δ 6.81 (s, 3H), 3.62 (t, J=6.3 Hz, 6H), 2.57 (t, J=7.5 Hz, 6H), 1.53-1.70 (m, 12H), 1.38 (m, 6H) ppm; $^{13}$C NMR (75 MHz, CDCl$_3$) δ 142.5, 126.1, 63.1, 36.1, 32.9, 31.5, 25.7 ppm.

Example 3

Preparation of 1,3,5-tris-(5-bromopentyl)benzene 1,3,5-tris-(5-hydroxypentyl)benzene (2.83 g, 8.41 mmol) and carbon tetrabromide (10.99 g, 32.80 mmol) were dissolved in dry methylene chloride (50 mL) and cooled to 0° C. Triphenylphosphine (9.03 g, 34.33 mmol) was added dropwise and the mixture was stirred for 30 minutes at 0° C. The mixture was poured into hexanes (250 mL), filtered through a short silica gel column and washed with ethyl acetate/hexanes (1/4). The combined organic solvents were evaporated to dryness under reduced pressure. The resulting residue was purified by column chromatography (hexanes:ethyl acetate 8:1) to afford 4.08 g of 1,3,5-tris-(5-bromopentyl)-benzene. Yield 92%. $^1$H NMR (300 MHz, CDCl$_3$) δ 6.81 (s, 3 h), 3.41 (t, J=6.9 Hz, 6H), 2.60 (t, J=7.5 Hz, 6H), 1.88 (m, H), 1.45 (m, 6H) ppm; $^{13}$C NMR (75 MHz, CDCl$_3$) δ 142.4, 126.1, 35.9, 34.2, 32.9, 30.9, 28.2 ppm.

Example 4

Preparation of 1,3,5-tris-[5-(1-quinolinium)pentyl]benzene tribromide

A mixture of 1,3,5-tris-(5-bromopentyl)benzene (251 mg, 0.48 mmol) and quinoline (930 mg, 7.20 mmol) was heated at 60-70° C. for 12 hours. The resultant mixture was washed with diethyl ether and then dissolved in water (15 mL), the aqueous solution was washed with diethyl ether (30 mL×5), then lyophilized to afford 390 mg of 1,3,5-tris-[5-(1-quinolinium)pentyl]-benzene tribromide. Yield 89%. $^1$H NMR (300 MHz, CD$_3$OD) δ 9.46 (dd, J=6.0, 1.5 Hz, 3H), 9.22 (d, J 8.4 Hz, 3H), 8.57 (d, J=9.0 Hz, 3H), 8.45 (dd, J=8.4, 1.5 Hz, 3H), 8.30 (m, 3H), 8.02-8.14 (m, 6H), 6.8 (s, 3H), 5.11 (t, 7.5 Hz, 6H), 2.56 (t, J=7.5 Hz, 6H), 2.14 (m, 6H), 1.69 (m, 6H), 1.52 (m, 6H) ppm; $^{13}$C NMR (75 MHz, CD$_3$OD) δ 150.3, 148.9, 143.4, 139.4, 137.3, 132.2, 131.8, 131.4, 127.2, 123.1, 119.9, 59.4, 36.7, 32.3, 31.1, 27.3 ppm.

Example 5

Figure 1:
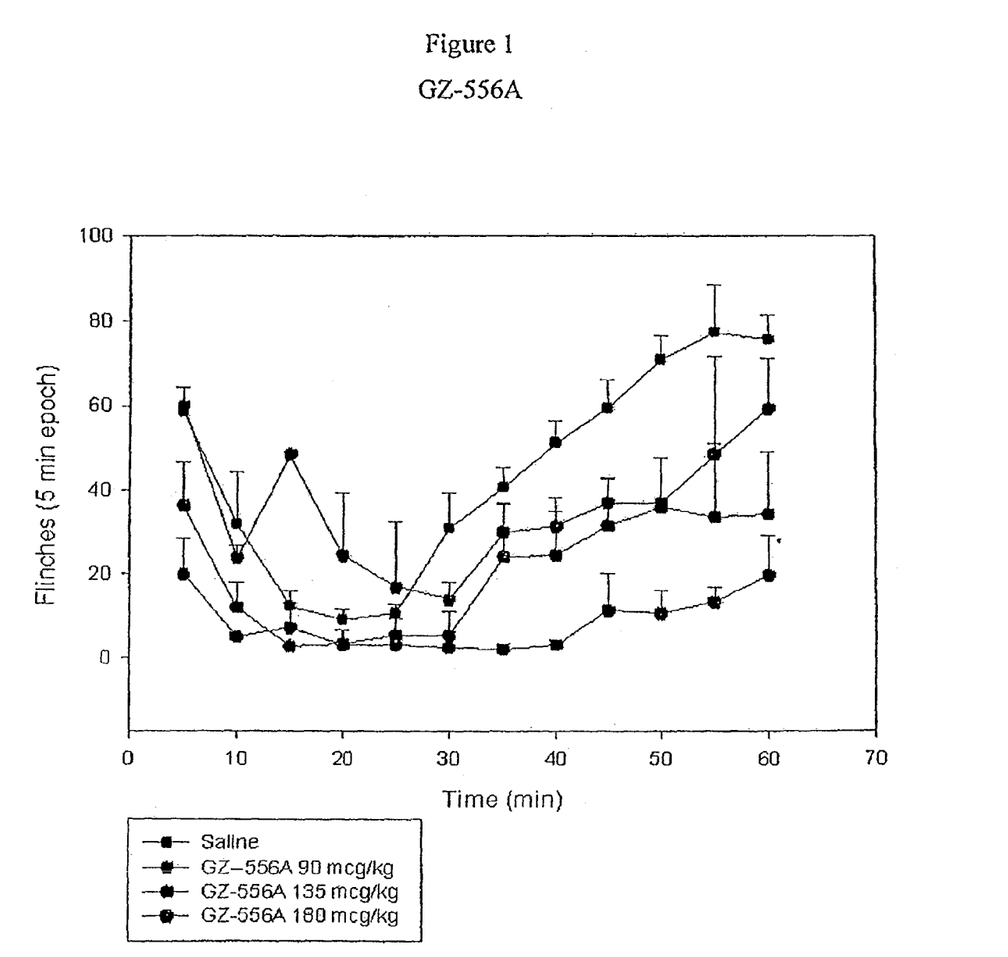
FIG. 1 shows the time curve of the effect of GZ-556A in the Rodent Formalin Tonic Pain model following intraperitoneal administration. Data are mean±SEM, n=3.
Figure 2:
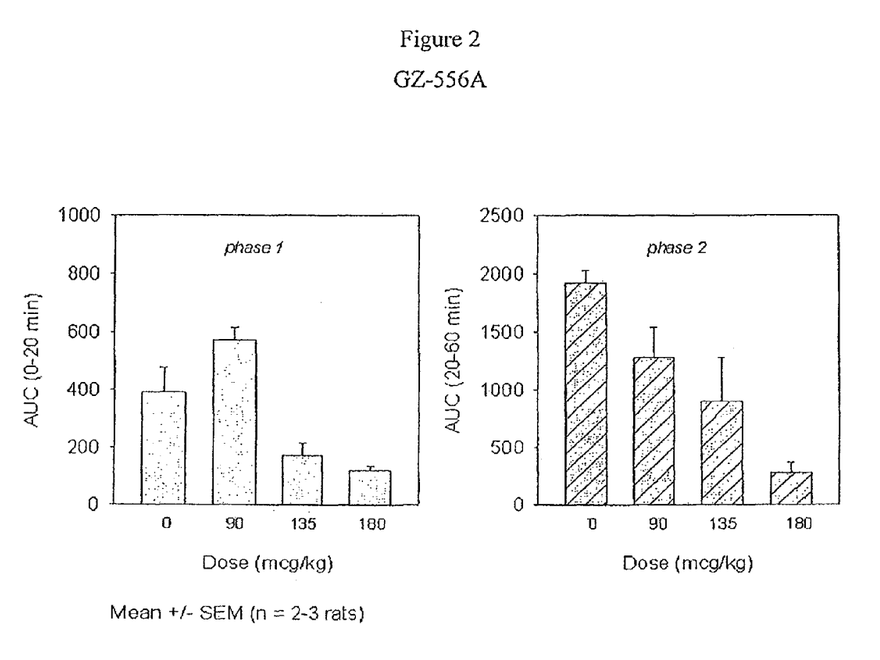
FIG. 2 shows the dose response of the effect of GZ-556A in Phase 1 and 2 of the Rodent Formalin Tonic Pain model following intraperitoneal administration. Data are mean±SEM, n=3.

A rat model of tonic inflammatory pain (the formalin test) was used in this study (Wheeler-Aceto and Cowan, 1991). Fifty μl of formalin (5%) was injected subcutaneously (SC) into the dorsal surface of the left hind paw. This procedure typically produces a biphasic behavioral response consisting of flinching, lifting and licking. The first phase (0-10 min) is thought to result from direct stimulation of nociceptors (nociceptive pain) whereas the second phase (20-60 min) is thought to involve central sensitization. Rats (4-8/dose/treatment) were pretreated 15 min prior to formalin (SC) injection with GZ-556A (90-180 mg/kg) administered by the IP route. Saline served as control. Incidences of formalin-induced flinching were counted continuously in 5 min intervals for 60 min. Each rat received only one treatment. The results are presented in FIGS. 1 and 2.

It will be appreciated that, although specific embodiments of the invention have been described herein for purposes of illustration, various modifications can be made without departing from the spirit and scope of the invention. All such modifications and variations are intended to be included herein within the scope of this disclosure and the present invention and protected by the following claims.

What is claimed is:

1. A method for treating neuropathic pain resulting from damage to the peripheral nervous system, comprising administering to a mammalian subject in need thereof a therapeutically effective amount of a compound of Formula (I):

wherein
the three side chains attached to the phenyl ring are connected to the 1, 3 and 5 positions of the phenyl ring;
m1, m2 and m3 are each 0;
n1, n2, and n3 are each 3;
$X^{1\ominus}$, $X^{2\ominus}$, and $X^{3\ominus}$ are each independently an organic or inorganic anion;
$L^1$, $L^2$ and $L^3$ are each —CH$_2$—CH$_2$—;
$R^1$, $R^2$, and $R^3$ are each quinolinium or isoquinolinium and attached to $(CH_2)_{n1}$, $(CH_2)_{n2}$, or $(CH_2)_{n3}$ at the quaternized nitrogen of the quinolinium or isoquinolinium.

2. The method of claim 1, wherein the compound of Formula (I) is 1,3,5-tris-[5-(1-quinolinium)-pentyl]-benzene tribromide.

3. The method of claim 1, wherein the pain is chronic.

4. The method of claim 1, wherein the pain is cancer-related pain.

5. The method of claim 1, wherein the pain is non-malignant pain.

6. A method for treating inflammatory pain resulting from activation of peripheral nociceptor, comprising administering to a mammalian subject in need thereof a therapeutically effective amount of a compound of Formula (I):

wherein
the three side chains attached to the phenyl ring are connected to the 1, 3 and 5 positions of the phenyl ring;
m1, m2 and m3 are each 0;
n1, n2, and n3 are each 3;
$X^{1\ominus}$, $X^{2\ominus}$, and $X^{3\ominus}$ are each independently an organic or inorganic anion;
$L^1$, $L^2$ and $L^3$ are each —CH$_2$—CH$_2$—;
$R^1$, $R^2$, and $R^3$ are each quinolinium or isoquinolinium and attached to $(CH_2)_{n1}$, $(CH_2)_{n2}$, or $(CH_2)_{n3}$ at the quaternized nitrogen of the quinolinium or isoquinolinium.

7. The method of claim 6, wherein the compound of Formula (I) is 1,3,5-tris-[5-(1-quinolinium)-pentyl]-benzene tribromide.

* * * * *